United States Patent [19]

Krystosek et al.

[11] Patent Number: 5,264,343
[45] Date of Patent: Nov. 23, 1993

[54] METHOD FOR DISTINGUISHING NORMAL AND CANCER CELLS

[75] Inventors: Alphonse Krystosek; Theodore T. Puck, both of Denver, Colo.

[73] Assignee: Eleanor Roosevelt Institute, Denver, Colo.

[21] Appl. No.: 575,900

[22] Filed: Aug. 31, 1990

[51] Int. Cl.$^5$ .................. C12Q 1/68; C12Q 1/48; C12Q 1/34; C12P 19/34

[52] U.S. Cl. ............................. 435/6; 435/15; 435/18; 435/91.2

[58] Field of Search ............... 435/6, 15, 18, 91, 810; 536/27, 28, 23.1; 935/77, 78

[56] References Cited

U.S. PATENT DOCUMENTS

| | | | |
|---|---|---|---|
| 4,707,352 | 11/1987 | Stavrianpoulos | 424/1.1 |
| 4,707,440 | 11/1987 | Stavrianopoulos | 435/6 |
| 4,711,955 | 12/1987 | Ward et al. | 536/29 |
| 4,746,604 | 5/1988 | Mowshowitz | 435/7 |
| 4,755,458 | 7/1988 | Rabbani et al. | 435/5 |
| 4,767,609 | 8/1988 | Stavrianpoulos | 424/1.1 |
| 4,772,548 | 9/1988 | Stavrianpoulos | 435/5 |
| 4,843,122 | 6/1989 | Stavrianopoulos | 525/61 |
| 4,849,208 | 7/1989 | Stavrianopoulos | 424/1.1 |
| 4,849,505 | 7/1989 | Stavrianopoulos | 530/300 |
| 4,889,798 | 12/1989 | Rabbani | 435/6 |
| 4,894,325 | 1/1990 | Englehardt et al. | 435/6 |
| 4,943,523 | 7/1990 | Stavrianopoulos | 435/7 |

OTHER PUBLICATIONS de Graaf, A., et al., "Three-Dimensional distribution of DNase I-sensitive chromatin regions in interphase nuclei of embryonal carcinoma cells", *European Journal of Cell Biology* (1990), vol. 52, pp. 135-141.

Enzo Diagnostics, Inc., Product Catalog (1988).

Hsie, A. W., and Puck, T. T. "Morphological Transformation of Chinese Hamster Cells by Dibutyryl Adenoisine Cyclic 3':5'-Monophosphate and Testosterone", *Proc. Natl. Acad. Sci.*, USA 68:358-361, (1971).

Bunn, P. A., Dienhart, D. G., Chan, D. Puck, T. T., Tagawa, M., Jewet, P. B., and Braunschweigher, E., "Neuropeptide Stimulation of Calcium Flux in Human Cancer Cells: Delineation of Alternative Pathways" *Proc. Natl. Acad. Sci.* USA 87:2162-2166, (1990).

Porter, K., Puck, T. T., Hsie, A. W., and Kelley, D., "An Electron Microscope Study of the Effects of Dibutyryl Cyclic AMP on Chinese Hamster Ovary Cells", *Cell* 2:145-158, (1974).

Puck, T. T. "Studies in Mammalian Cell Regulation: Cell Surface Antigens and the Action of Cyclic AMP"; pp. 171-180, P. Ts'o, editor; Elsevier North-Holland Biomedical Press, Amsterdam, N.Y. (1977).

Gabrielson, E. G., Scoggin, C. and Puck, T. T. "Phosphorylation Changes Induced by cAMP Derivatives in the Cho Cell and Selected Mutants"; *Exp. Cell Res.* 142:63-68 (1982).

Chan, D., Goate, A., and Puck, T. T., "Involvement of Vimentin in the Reverse Transformation Reaction", *Proc. Natl. Acad. Sci.* USA 86:2747-2751 (1989).

Miranti, C., and Puck, T. T., "Gene Regulation in Reverse Transformation: Cyclic AMP-Induced Actin Homolog in CHO Cells", *Somat. Cell Molec.d Genet.* 16:67-78 (1990).

Kerem, B. S., Goiten, R., Diamond, G., Cedar, H., and Marcus, M., "Mapping of DNAse 1 Sensitive Regions on Mitotic Chromosomes", *Cell* 38:493-499 (1984).

(List continued on next page.)

Primary Examiner—Stephanie W. Zitomer
Attorney, Agent, or Firm—Beveridge, DeGrandi, Weilacher & Young

[57] ABSTRACT

A method of electing the presence or absence of exposed nuclear DNA is described. Cells are reacted with a reaction composition comprising DNA polymerase I, DNase I, and the nucleotides dATP, dCTP, dGTP, and dTTP or dUTP, at least one of said nucleotides being biotin labeled. Biotin labeled nucleotides incorporated in exposed DNA are detected. Also described is a kit useful for detecting the presence or absence of exposed DNA in cells.

20 Claims, 4 Drawing Sheets

OTHER PUBLICATIONS

Hutchison, N., and Weintraub, H. "Localization of DNAase 1-Sensitive Sequences to Specific Regions of Interphase Nuclei", *Cell* 43:471–482 (1985).

Schonberg, S., Patterson, D., and Puck, T. T., "Resistance of Chinese Hamster Ovary Cell Chromatin to Endonuclease Digestion", *Exp. Cell Res.* 145:57–62 (1983).

Ashall, F., Sullivan, N., and Puck, T. T., "Specificity of the cAMP-Induced Gene Exposure Reaction in CHO Cells"; *Proc. Natl. Acad. Sci.* USA 85:3908–3912 (1988).

Ashall, F., and Puck, T. T., "Cytoskeletal Involvement in cAMP-Induced Sensitization of Chromatin to Nuclease Digestin in Transformed Chinese Hamster Ovary K1 Cells", *Proc. Natl. Acad. Sci.* USA 81:5145–5149 (1984).

Tjio, J. H., and Puck, T. T., "Genetics of Somatic Mammalian Cells", *J. Exp. Med.* 108:259–268 (1958).

Hamilton, W. G., and Ham, R. G. "Clonal Growth of Chinese Hamster Cell Lines In Protein-Free Media", In Vitro 13:537–547 (1977).

Capco, D. G., Wan, K. M., and Penman, S., "The Nuclear Matrix: Three-Dimensional Architecture and Protein Composition", Cell 29:847–858 (1982).

Krystosek, A., and Puck, T. T., "Genome Exposure in Reverse Transformation", *J. Cell Biol.* 109:231a (1989).

Larsen, A., and Weintraub, H., "An Altered DNA Conformation Detected by S1 Nuclease Occurs at Specific Regions in Active Chick Globin Chromatin", *Cell* 29:609–622 (1982).

Weintraub, H., and Groudine, M., "Chromosomal Subunits in Active Genes Have an Altered Conformation", *Science* 193:848–856 (1976).

Garel, A., and Axel, R., "Selective Digestion of Transcriptionally Active Ovalbumin Genes From Oviduct Nuclei" *Proc. Natl. Acad. Sci.* USA 73:3966–3970, (1976).

Wu, C., Wong, Y. C., and Elgin, S. C. R., "The Chromatin Structure of Specific Genes: II. Disruption of Chromatin Structure During Gene Activity", *Cell* 16:807–814 (1979).

Puck, T. T., Krystosek, A., and Chan, D., "Genome Regulation in Mammalian Cells", *Somat. Cel Mol. Genet.* 16:257–265 (1990).

Arechaga, J., Diaz, J., Silio, M. and Bahr, G. F., "Mass and Molecular Weight of Isolated Nuclear Rings", Biol. Cell 68:13–20 (1990).

Franke, W. W., "Nuclear Lamins and Cytoplasmic Intermediate Filament Proteins: A Growing Multigene Family", *Cell* 48:3–4 (1987).

Bennett, M. D. "Ordered Disposition of Parental Genomes and Individual Chromosomes in Reconstructed Plant Nuclei, and Their Implications", *Somat. Cell Mol. Genet.* 13:463–466 (1987).

Matsumoto, L. H., "Enrichment of Satellite DNA on the Nuclear Matrix of Bovine Cells", *Nature* 294:481–482 (1981).

Ellison, J. R. and Howard, G. C., "Non-Random Position of the A-T Rich DNA Sequences in Early Embryos of Drosophila Virilis", Chromosoma 83:555–561 (1981).

Ciejek, E. M., Tsai, M. J., and O'Malley, B. W., "Actively Transcribed Genes Are Associated with the Nuclear Matrix", Nature 306:607–609 (1983).

Vogelstein, B., Pardoll, D. M., and Coffey, D. S., "Supercoiled Loops and Eucaryotic DNA Replication", Cell 22:79–85 (1980).

Law, M. L., Gao, J., & Puck, T. T., "A Nuclear Protein Associated With Human Cancer Cells Binds Preferentially to a Human Repetitive DNA Sequence", *Proc. Natl. Acad. Sci. USA* 86:8472–8476 (1989).

Rae, P. M. M., and Franke, W. W., "The Interphase Distribution of Satellite DNA-Containing Heterochromatin in Mouse Nuclei", *Chromosoma* 39:443–456 (1972).

Maniatis et al., Molecular Cloning, A Lab. Man. 1982 (pp. 109–111).

FIG. IA  FIG. IB
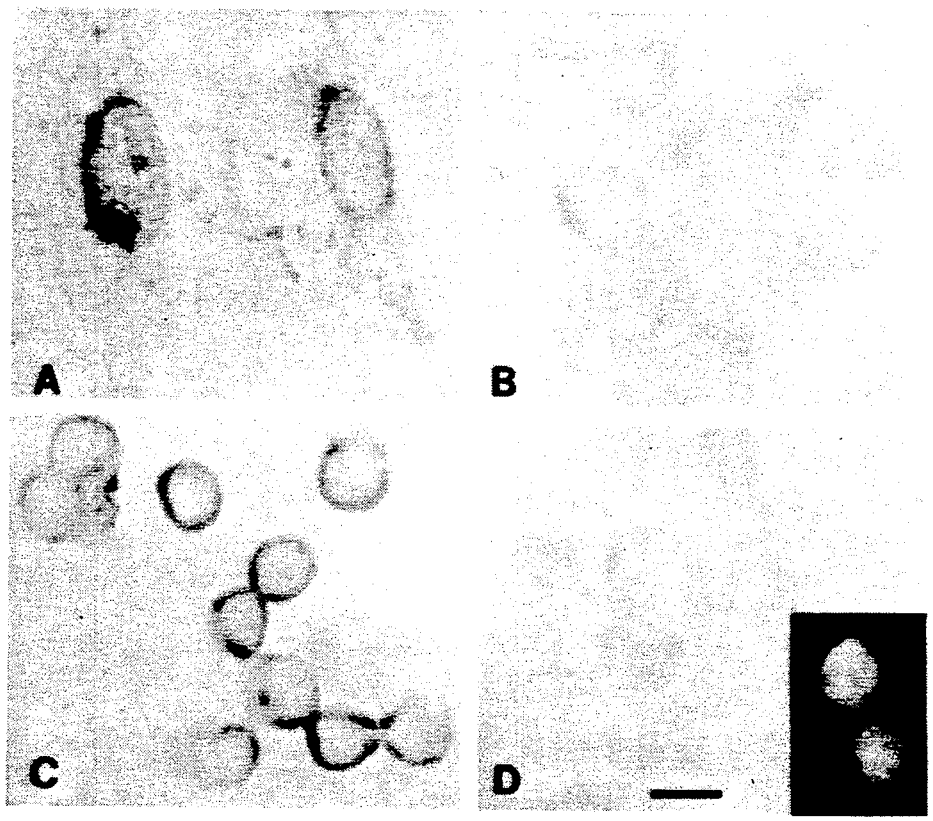
FIG. IC  FIG. ID

FIG. 3A
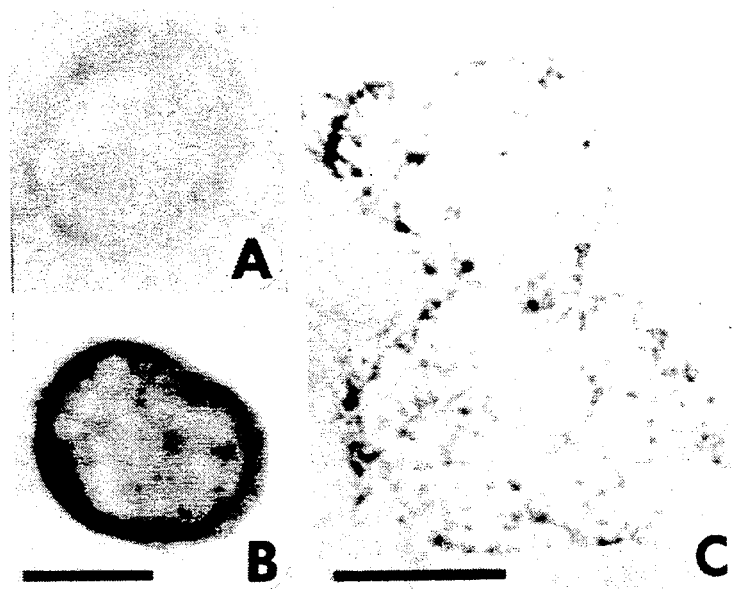
FIG. 3B  FIG. 3C
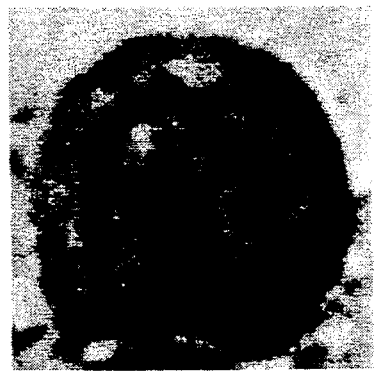
FIG. 4

FIG. 5A  FIG. 5B
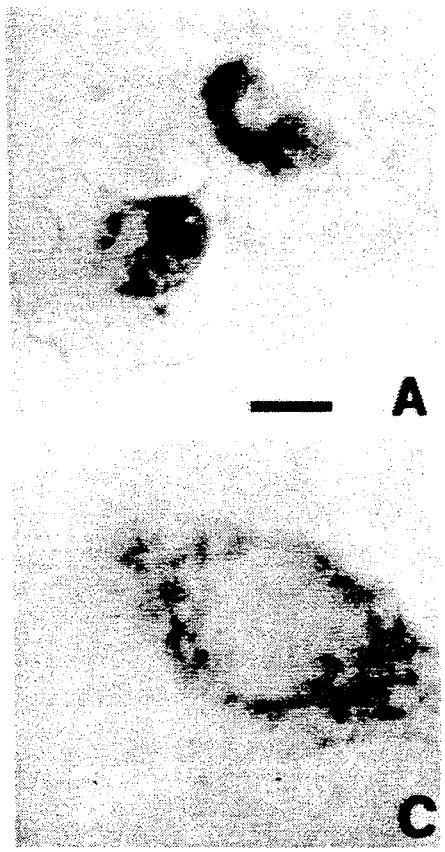 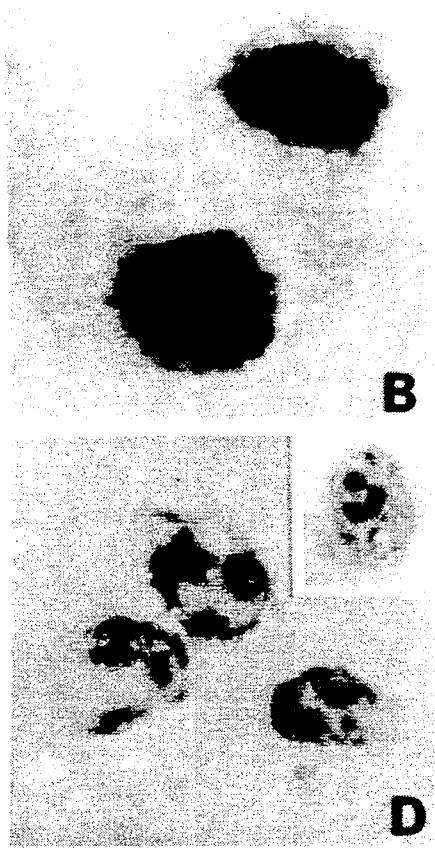
FIG. 5C  FIG. 5D

METHOD FOR DISTINGUISHING NORMAL AND CANCER CELLS

BACKGROUND OF THE INVENTION

The present invention concerns the detection of exposed nuclear DNA. More especially, this invention concerns a method to diagnose cancer by determining the presence or absence of exposed nuclear DNA in cells and to monitor the progress of cancer therapy. The present invention also concerns a kit useful for detecting the presence or absence of exposed nuclear DNA.

Reverse transformation is a reaction in which malignant cells are restored to a normal phenotype in response to particular agonists as in the CHO-K1 cell treated with cyclic AMP derivatives. See Hsie, A. W., and T. T. Puck, *Proc. Natl. Acad. Sci. USA* (1971), volume 68, pages 358-361. It involves a succession of complex metabolic changes varying from early alterations in calcium ion dynamics occurring during the first minute, to changes in membrane and cytoskeletal structures, and protein syntheses and phosphorylations which extend over a period of more than 48 hours. See Bunn, P. A., D. G. Dienhart, D. Chan, T. T. Puck, M. Tagawa, P. B. Jewett, and E. Braunschweiger, *Proc. Natl. Acad. Sci. USA* (1990), volume 87, 2162-2166; Porter, K. R., T. T. Puck, A. W. Hsie, and D. Kelley, *Cell* (1974), volume 2, pages 145-158; Puck, T. T., *The Molecular Biology of the Mammalian Genetic Apparatus* (1977), pages 171-180; Gabrielson, E. G., C. Scoggin, and T. T. Puck, Exp. Cell Res. (1982), volume 142, pages 63-68; Chan, D., A. Goate, and T. T. Puck, Proc. Natl. Acad. Sci. USA (1989), volume 86, pages 2747-2751; and Miranti, C., and T. T. Puck, *Somat Cell Molec. Genet.* (1990), volume 16, pages 67-78. Ultimately, the pathway must result in specific changes in nuclear gene activity which restore specific differentiation and growth control properties to the affected cells. Through modified techniques developed for demonstrating sensitivity to hydrolysis of nuclear DNA, it has previously been demonstrated that an increase in DNA sensitivity to hydrolysis which affects specific nuclear genes and involves a substantial fraction of the genome occurs in the course of Reverse Transformation See Kerem, B., R. Goitein, G. Diamond, H. Cedar, and M. Marcus, *Cell* (1984), volume 38, pages 493-499; Hutchison, N., and H. Weintraub, Cell (1985), volume 43, pages 471-482; Schonberg, S., D. Patterson, and T. T. Puck, *Exp. Cell Res.* (1983), volume 145, pages 57-62; and Ashall, F., N. Sullivan, and T. T. Puck, *Proc. Natl. Acad. Sci. USA* (1988), volume 85, pages 3908-3912. This large-scale increase in DNase I sensitivity of chromatin following treatment of cells with specific reverse transformation agents is now termed genome exposure It has been demonstrated that cytoskeletal integrity is required for this reaction and that the degree of increased exposure achieved in reverse transformation resembles that in normal cells. See Ashall, F., and T. T. Puck, *Proc. Natl. Acad. Sci. USA* (1984), volume 81, pages 5145-5149.

The present invention demonstrates that cancer cells lack DNase I-sensitive regions of the genome which in normal cells are preferentially localized at the nuclear periphery. Thus, the present invention may be utilized in the diagnosis of cancer (e.g., in pap smears) and to monitor the progress of cancer therapy. Since the present invention demonstrates that normal cells have a DNase I-sensitive region localized at the nuclear periphery, the present invention might be utilized to investigate pathological conditions which result in a compromise in nuclear function (e.g., genetic diseases, neurodegenerative diseases).

SUMMARY OF THE INVENTION

It is an object of the present invention to provide a method for the detection of exposed nuclear DNA in cells. It is a further object to provide a method to diagnose cancer by determining the presence or absence of exposed DNA in cells. It is also an object to provide a kit useful for detecting the presence or absence of exposed nuclear DNA in cells.

In one variation of the method to detect exposed nuclear DNA in cells, the method following steps:

(a) reacting cells to be tested, such as cells suspected of being cancerous, with a reaction composition comprising DNA polymerase I, DNase I, and at least one member selected from the group consisting of the nucleotides dATP, dCTP, dGTP, dTTP and dUTP, at least one of said nucleotides being biotin labeled; and (b) detecting the presence of biotin incorporated in exposed DNA.

In one variation of the method, the reaction composition is present as a reaction mixture.

In one variation of the method, the biotin labeled nucleotide is biotin-11-dUTP.

In another variation of the method, the biotin incorporated in exposed DNA can be detected by a method comprising the following steps:

(a) reacting cells which have been reacted with the reaction composition with antibiotin antibodies in order to obtain a complex of incorporated biotinylated nucleotides and antibiotin antibodies;

(b) reacting cells so treated with alkaline phosphatase conjugated antibodies directed against antibiotin antibodies in order to obtain a complex of incorporated biotinylated nucleotides, antibiotin antibody, and alkaline phosphatase conjugated antibodies directed against antibiotin antibodies; and (c) reacting cells so treated with amplification reagents to obtain a color reaction with alkaline phosphatase conjugated antibodies directed against antibiotin antibodies which are specifically bound to incorporated biotinylated nucleotides.

In yet another variation of the method, the biotin incorporated in exposed DNA is detected by a method comprising the following steps:

(a) reacting cells which have been reacted with the reaction composition with streptavidin-alkaline phosphatase conjugate in order to obtain a complex of incorporated biotinylated nucleotides and streptavidin-alkaline phosphatase conjugates; and (b) reacting cells so treated with amplification reagents to obtain a color reaction with streptavidin-alkaline phosphatase conjugates which are specifically bound to incorporated biotinylated nucleotides.

In one variation, the amplification reagents comprise nitroblue tetrazolium and 5-bromo-4-chloro-3 indolyl phosphate.

In one variation, a kit useful for detecting the presence or absence of exposed nuclear DNA in cells comprises the following:

(a) DNA polymerase I, DNase I, least one member selected from the group consisting of the nucleotides dATP, dCTP, dGTP, dTTP and dUTP, at least one of said nucleotides being biotin labeled; and (b) a detection means for detecting the presence of biotin labeled nucleotides incorporated in exposed nuclear DNA.

The in situ methodology herein described has several advantages over gel electrophoretic methods. It not only provides nuclear localization of the exposed genes but requires only a few thousand cells for each determination so that the methodology can now be applied to a wide variety of different normal and pathologic mammalian tissues.

BRIEF DESCRIPTION OF THE DRAWINGS

The present invention will be further understood with reference to the drawings, wherein FIG. 1 is a photomicrograph showing a comparison of genome exposure in normal Chinese hamster ovary fibroblasts, transformed and reverse transformed CHO-K1 cells. Assays were carried out as described in the text. A) normal, early passage Chinese hamster fibroblasts; B) transformed CHO-K1 cells: C) 8BrcAMP treated CHO-K1; D) as in C except that no DNase I was included in the assay. Inset in D shows the typical appearance of CHO-K1 stained with DAPI, demonstrating that DNA is distributed reasonably uniformly throughout the nucleus. Bar=10 micrometers.

FIG. 3 is a photomicrograph showing nuclear matrix localization of labeled chromatin. Matrices were prepared using the CSK (panels A, B) and CSK-AS (panel C) buffers of Capco et al. See Capco, D. G., K. M. Wan, and S. Penman, In Vitro (1982), volume 29, pages 847-858. The micrographs show the labeling pattern of 8BrcAMP treated CHO-K1, except A which is untreated. Matrices not treated with exogenous DNase I did not develop color (not shown), indicating that they do not contain significant amounts of endogenous nicks. Bars=10 micrometers.

FIG. 4 is a photomicrograph showing in situ nick translation of a blood lymphocyte from a cytospin preparation. Ring labeling pattern typical of normal cells is seen. Cell diameter is 10 micrometers.

FIG. 5 is a photomicrograph showing experimental variation of labeling pattern The patterns are described in the text. A) EcoR1; B) MspI 1; C) DNase I, 20 min; D) 60 min nicking incubation with DNase I followed by a 1 min. incorporation period. Inset in D shows the location of centromeric heterochromatin visualized by interphase C banding. Giemsa stain. See Rae. P. M. M., and W. W. Franke, Chromosoma (1972), volume 39, pages 443-456 Bar=10 micrometers.

DETAILED DESCRIPTION OF THE INVENTION

Figures 2A, 2B, 2C:
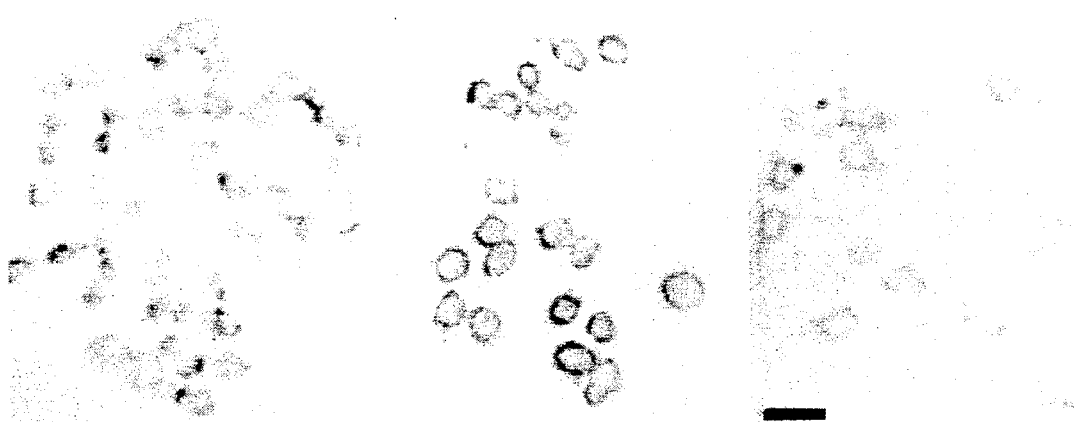
FIG. 2 is a photomicrograph showing cytoskeletal involvement in genome exposure Cells were grown for 3 days without additions (left) or in the presence of 0.5 mM 8BrcAMP (center and right) and with 2.5 micromoles colcemid for 2.5 hrs prior to fixation for assay (right). The typical labeling pattern of reverse transformed cells is eliminated in the presence of the microtubule-disrupting drug. Bar=20 micrometers.

In carrying out the invention, the following cells and reagents are utilized: CHO-K1 is a sub-clone of the transformed Chinese hamster ovary cell isolated in 1958. See Tjio, J. H., and T. T. Puck, J. Exp. Med. (1958), volume 108, pages 259-268 An early passage line of the non-immortalized CHO-784 cell was used as a normal fibroblast for comparison studies. Cells were grown in F12 medium supplemented with 7% fetal calf serum and maintained at 37° C. in a humidified 5% $CO_2$ atmosphere. For some experiments a defined medium (MCDB 302) supplemented with insulin and transferrin was used as previously described. See Ashall, F., N. Sullivan, and T. T. Puck, Proc. Natl. Acad. Sci. USA (1988), volume 85, pages 3908-3912; and Hamilton, W. G., and R. G. Ham, In Vitro (1977), volume 13, pages 537-547. Other standard media, well known in the art, may be used.

The sources of special reagents were as follows 8BrcAMP (Boehringer Mannheim Biochemicals); biotinylated nucleotides (Enzo Biochemicals); restriction enzymes, DNA polymerase I and klenow fragment (Promega); DNase I (Bethesda Research Laboratories); antibodies, DAPI, 4,6 diaminidino-2 phenyl indole, a fluorescent DNA-binding dye, and isobutyl methyl xanthine (Sigma Chemicals Co.); streptavidin-alkaline phosphatase conjugate (Tago Immunochemicals); forskolin (CalBiochem).

Incorporation Step: The following in situ nick translation was utilized: Round glass coverslips (18 or 25 mm, #2 thickness) were precoated with poly-D-lysine (30 min, 100 micrograms/ml) to increase adhesiveness. Approximately 3000 cells were seeded onto coverslips placed in 35 mm tissue culture dishes containing 2 ml of F12 medium containing 7% fetal calf serum and were used for assay at the indicated times of growth. Coverslips were rinsed twice in PBS and then fixed in cold 20:1 methanol:acetic acid for 20 minutes followed by rinses with PBS to neutralize the pH. See Hutchison, N., and H. Weintraub, Cell (1985), volume 43, pages 471-482. The reaction mixture utilized contains 50 mM Tris-HCl, pH 7.9, 5 mM $MgCl_2$, 10 mM 2-beta-mercaptoethanol, 50 micrograms/ml acetylated bovine serum albumin, 4 units E. coli DNA polymerase (or Klenow enzyme), 100 micromoles dATP, dCTP, dGTP and 5 micromoles biotin-11-d-UTP (as dTTP analogue). Alternatively, biotin-16-dUTP can be utilized (the 11 and 16 referring to the length of spacer arms in the molecule which are not relevant to the way the chemical is used in the present invention). All four nucleotides (i.e., dATP, dCTP, dGTP, and dTTP) must be used, at least one of which is biotin labelled; biotin labeled dUTP can replace dTTP. DNase I was included in this mix at 1-33 ng/ml or omitted for control purposes (One ng/ml is equivalent to approximately 0.01 units/ml.) Alternatively, micrococcal nuclease or nuclease S1 from Aspergillus oryzae may be utilized in place of DNase I. The reaction mixture was applied to cells by sandwiching 10 microliters between the coverslip and a clean glass slide. Reactions were carried out at room temperature (22°-27° C.) for 1 to 5 minutes and were stopped by immersing the coverslips in a 20 mM EDTA solution, pH 8.0. Alternatively, the reaction can be stopped by multiple rinses of the coverslips in buffer in order to dilute the assay components to levels which are no longer active.

To summarize nick translation: DNA is "nicked" by DNase I. DNA polymerase I catalyzes the sequential addition of nucleotide residues to the 3'-hydroxyl terminus of a nick while simultaneously eliminating nucleotides from the 5'-phosphoryl terminus, the nick is translated linearly along the DNA strand. When biotinylated nucleotides are present, the pre-existing unmodified nucleotides in the DNA strand are replaced by biotinylated analogs.

Alternatively, digoxigenin labeled nucleotides (e.g., digoxigenin-11-dUTP) could be utilized in place of biotin labeled nucleotides. Alkaline phosphatase conjugated sheep anti-digoxigenin antibodies would subsequently be used in the detection step.

Detection Step: The two detection systems for incorporated biotin which were utilized are based on amplification reagents giving a colored reaction product as the final signal Coverslips were washed in a buffer of moderate ionic strength (buffer 1: 100 mM Tris-HCl, pH 7.5; 150 mM NaCl) following the incorporation step and were then incubated for 30 min in buffer 1 containing 100 micrograms/ml acetylated bovine serum albumin and affinity reagents titrated to levels minimizing background binding. The affinity reagents can be either streptavidin-alkaline phosphatase or goat antibiotin antibody followed by alkaline phosphatase conjugated antigoat IgG. Other affinity reagents, well known in the art, can be utilized.

Goat antibiotin antibody was used at 1:400 (15-20 microliters/coverslip) followed by rabbit antigoat IgG conjugated with alkaline phosphatase (1:500)(10-15 microliters). Other combinations of primary and secondary antibodies, known in the art, can be utilized. Fluorescent, enzymatic, metallic and isotopic tags can be utilized. Three washing steps with buffer 1 were interposed between antibody incubations and color development.

Alternatively, streptavidin-alkaline phosphatase conjugate was used at 1:10,000 as a direct biotin binding ligand. In the present invention, a preincubation of the coverslip with unconjugated streptavidin (10 micrograms/ml) for 20 minutes at room temperature (21°-27° C.) prior to the incorporation incubation was necessary to prevent a nonspecific absorption to cytoplasmic structures. Other direct biotin binding ligands can be utilized: streptavidin or avidin (especially avidin DN) conjugated with horseradish peroxidase, FITC (a fluorescent dye conjugate), sulforhodamine 101 (Texas Red), phycoerythrin, rhodamine, fluorescein, etc. FITC conjugates are viewed directly with epifluorescence microscopy to give a colored signal Peroxidase is developed with a color product reaction analogous but not identical to the schemes for phosphatase. Avidin is a biotin binding protein from chicken eggs, whereas streptavidin is a biotin binding protein from *Streptomyces avidinii*. The high affinity binding to biotin is analogous to the antigen-antibody coupling.

To develop color in the two detection systems, coverslips with bound conjugates were rinsed briefly in alkaline buffer (Tris-HCl 100 mM; 100 mM NaLl, 50 mM MgCl$_2$, pH 9.5) and the phosphatase reaction was developed in this buffer containing 40 mM of nitroblue tetrazolium and 40 mM 5-bromo-4-chloro-3 indolyl phosphate (alternatively, it may be possible to utilize the chromogenic phosphatase substrate p-nitrophenyl phosphate which can be enzymatically cleaved by alkaline phosphatase to yield soluble colored p-nitrophenol). Slides were monitored microscopically for the deposition of a purple reaction product at incorporation sites and the reaction was stopped prior to overdevelopment (5-60 minutes) by immersion in stop buffer (10 mM Tris-HCl, 5 mM EDTA; pH 8.0). Coverslips were air dried and mounted onto slides with Permount for evaluation and photomicroscopy.

Reverse transformation of CHO-K1 cells was effected by treatment with 0.5 mM 8BrcAMP or by 10 micromoles forskolin, a cAMP inducer, for 1-7 days (preferably 72 hours).

The following articles are incorporated by reference for descriptions of standard materials and methods known in the art: (1) Hutchison, N., and H. Weintraub, "Localization of DNAase I-Sensitive Sequences to Specific Regions of Interphase Nuclei," Cell (1985), volume 43, pages 471-482; (2) Kerem, B., R. Goitein, G. Diamond, H. Cedar, and M. Marcus, "Mapping of DNAase I Sensitive Regions on Mitotic Chromosomes," Cell (1984), volume 38, pages 493-499; (3) Ashall, F., N. Sullivan, and T. T. Puck, "Specificity of the cAMP-induced gene exposure reaction in C cells," Proc Natl. Acad. Sci. USA (1988), volume 85, pages 3908-3912; (4) Hamilton, W. G., and R. G. Ham, "Clonal Growth of Chinese Hamster Cell Lines in Protein-Free Media," In Vitro (1977), volume 13, pages 537-547; (5) Tjio, J. H., and T. T. Puck, "Genetics of Somatic Mammalian Cells," J. Exp. Med. (1958), volume 108, pages 259-268; (6) Schonberg, S., D. Patterson, and T. T. Puck, "Resistance of Chinese Hamster Ovary Cell Chromatin to Endonuclease Digestion," Exp. Cell Res. (1983), volume 145, pages 57-62; (7) Ashall, F., and T. T. Puck, "Cytoskeletal involvement in cAMP-induced sensitization of chromatin to nuclease digestion in transformed Chinese hamster ovary K1 cells," Proc. Natl Acad. Sci. USA (1984), volume 81, pages 5145-5149; (8) Krystosek, A., and T. T. Puck, "Genome Exposure in Reverse Transformation," J. Cell. Bio (1989), volume 109, page 231a; (9) Capco, D. G., K. M. Wan, and S. Penman, "The Nuclear Matrix: Three-Dimensional Architecture and Protein Composition," Cell (1982), pages 847-858; (10) Rae, P. M. M., and W. W. Franke, "The Interphase Distribution of Satellite DNA-Containing Heterochromatin in Mouse Nuclei," Chromosoma (1972), volume 39, pages 443-456; and (11) Larsen, A., and H. Weintraub, "An Altered DNA Conformation Detected by S1 Nuclease Occurs at Specific Regions in Active Chick Globin Chromatin," Cell (1982), volume 29, pages 609-622.

EXAMPLES

Comparison of normal, transformed and reverse transformed cells: Experiments were carried out in which the in situ method herein described for revealing the location of exposed DNA was applied to norma , transformed and reverse transformed Chinese hamster fibroblasts. Development of a color reaction with alkaline phosphatase conjugates specifically bound to incorporated biotinylated nucleotides marked the sites susceptible to nicking upon a brief treatment of fixed cells with exogenous DNase I. Typical results are presented in FIG. 1: (a) In FIG. 1A is shown the pattern produced by applying the in situ procedure to normal, early passage Chinese hamster ovary fibroblasts (CHO-784). These cells, both in the presence and absence of 8BrcAMP or of forskolin, revealed the same pattern, i.e. the presence of the digestion-sensitive chromatin densely distributed about the periphery of the nucleus. The peripherally distributed exposed DNA was punctuated by regions of higher and lower density; more sparse but definite exposed DNA regions were demonstrable in the inner portions of the nucleus. (b) Untreated, malignant CHO-K1 cells showed only a sparse, patchy or diffuse uptake of label which was not particularly associated with the nuclear periphery (FIG. 1B). (c) If the cells in (b) were pretreated for 3 days with 8BrcAMP, however, a pattern of DNA exposure was demonstrated consisting of a heavy band circling all or most of the nuclear periphery (FIG. 1C). As in untreated normal cells, the band in reverse transformed cells was not completely uniform but at high magnification revealed the presence of punctuate regions of higher density of the sensitive DNA. Minor amounts of labeled DNA also occurred in the nuclear interior and again showed discontinuities in the degree of labeling. Similar results were obtained when isolated nuclei rather than whole cells were employed. The similarity of results with fixed cells and with detergent extracted nuclei prepared with methods for electrophoretic gel analysis of DNA digestion suggest that the bulk method (i.e., the gel method) and the analytical method (i.e., the in situ method) measure aspects of the same phenomena of genome exposure See Schonberg, S., D. Patterson, and T. T. Puck, Exp. Cell Res. (1983), volume 145, pages 57-62; Ashall, F., N. Sullivan, and T. T. Puck, *Proc. Natl. Acad. Sci. USA* (1988), volume 85, pages 3908-3912; and Ashall, F., and T. T. Puck, *Proc. Natl. Acad. Sci. USA* (1984), volume 81, pages 5145-5149. FIG. 1D presents a situation exactly like that in FIG. 1C except that DNase I treatment was omitted from the procedure. The absence of any visible deposit demonstrates clearly that the effects obtained are due to the hydrolytic nicking of the DNA by the nuclease. The described differences between malignant and reverse transformed cells in color development intensity in the nuclear ring were consistently observed throughout the periods from early to late color formation in the course of the reaction.

The insert in FIG. 1D represents a picture of the total DNA fluorescence obtained by treatment of CHO-K1 cells with fluorescent dye (DAPI). Such cells, whether treated or untreated with cyclic AMP, reveal a reasonably homogenous distribution of DNA throughout the nucleus Thus, the peripheral ring shown in the nuclei of cyclic AMP-treated cells is not due to the existence of a pre-existing pattern in the distribution of total DNA but rather only of DNA sensitive to DNase I hydrolysis. These results demonstrate that in reverse transformed, but not in untreated CHO-K1 cells, the location and extent of the pattern of enzyme-accessible chromatin approaches that characteristic of normal fibroblasts.

The difference in sensitive chromatin structure in response to treatment with 8BrcAMP could often (14 of 22 comparisons) but not always be detected when the 8BrcAMP incubation period was reduced to 24 hours. The optimal incubation period is three days. Extending the time of treatment with 8BrcAMP from three to seven days with or without subculturing did not enhance the labeling pattern. After a three-day treatment of cells with 8BrcAMP, a further incubation for 4 hours in growth medium cyclic AMP caused the labeling profile to revert to the control pattern consistent with the previous observation of the phenotypic reversibility of the Reverse Transformation phenomenon. See Hsie, A. W., and T. T. Puck, *Proc. Natl. Acad. Sci. USA* (1971), volume 68, pages 358-361.

The effect of 8BrcAMP could be duplicated by treatment of cells with 10 micromoles forskolin plus $10^{-4}$ m isobutylmethylxanthine, an indication that the genome exposure is indeed responding to the elevation of intracellular cyclic AMP levels. Isobutylmethylxanthine is a phosphodiesterase inhibitor which inhibits cellular phosphodiesterase which would otherwise destroy cAMP; it therefore potentiates the effects of compounds which raise intracellular cAMP levels (such as forskolin which activates the enzyme which makes cAMP).

All of the following changes in conditions did not affect the difference in labeling between untreated and reverse transformed CHO-K1 cells: Growth on plastic rather than glass; use of defined serum-free medium rather than the standard growth medium; using separate, optimizing nicking and incorporation steps in the assays; carrying out the nick translation at 14° C.; use of biotin-11-dCTP; fixation of cells prior to assay with absolute methanol rather than 20:1 methanol : acetic acid; or subculturing of cells one day prior to assay so that control and treated cells were present as single cells or small groups rather than as a contiguous population.

Various experiments for control purposes assessed the specificity of both the incorporation and detection systems. No color development above background was observed in the absence of any of the following: DNase I, polymerase, biotinylated nucleotide, unlabeled nucleotides in the assay; primary or secondary affinity reagents in the detection steps; or 5-bromo-4-chloro-3 indolyl phosphate or NBT in the color reaction. Inclusion of a 100 fold excess of dTTP eliminated the biotin incorporation. Likewise, the detection conjugates showed specific competition, e.g. no color development occurred when streptavidin-alkaline phosphatase was use in the presence of a 100-fold excess of unconjugated streptavidin. Incorporated biotin could be released by a subsequent incubation with 1 microgram/ml DNase I, suggesting that the analog is in fact covalently bound into DNA.

Requirement for cytoskeletal integrity. If the in situ assay measures an aspect of the genome exposure reaction previously defined by the gel analysis it should also show the requirement for cytoskeletal integrity. See Ashall, F., and T. T. Puck, *Proc. Natl. Acad. Sci. USA* (1984), volume 81, pages 5145-5149. Experiments were carried out in which the CHO-K1 cells grown for 72 hours in the presence of 8BrcAMP were treated with 2.6 micromoles colcemid for 2½ hours prior to fixation for the in situ labeling assay. The presence of the colcemid largely eliminated the usual heavy labeling around the nuclear periphery observed in 8BrcAMP treated cells (FIG. 2). Similar results were obtained using 5 micromoles cytochalasin B in place of colcemid. In both cases the drug treated cells showed a markedly diminished labeling of the nuclear periphery as well as a decreased color intensity throughout the entire nucleus.

Association of DNase-I-sensitive chromatin with the insoluble matrix. Nuclear matrix/cytoskeletal preparations were prepared by salt and detergent extraction of CHO-K1 cells grown on coverslips following the procedure of Capco et al. See Capco, D. G., K. M. Wan and S. Penman, *Cell* (1982), volume 29, pages 847-858. When the nick translation procedure is preceded by extraction with moderate concentrations of salt the peripheral nuclear ring which differentiates the 8BrcAMP-treated from the untreated cell was left intact (FIG. 3, A and B). Use of a high salt extraction, however, which presumably removes many more protein constituents leaving the nuclear matrix behind, still left a clear difference between the control and reverse transformed cell, but the staining intensity of the latter was markedly diminished. In FIG. 3C is shown the result obtained from BrcAMP treated cells. Control cells similarly treated were completely blank. These experiments suggest that some of the DNA in the reverse transformed cell is intimately connected with the nuclear matrix. Of considerable interest are two other features. A punctate pattern of exposed DNA covered the outermost lamina of high salt-extracted matrices. Moreover, there was a definite suggestion of a linear pattern connecting the punctate deposits. A physical association of labeled DNA with the lamin polymer system is suggested.

Examination of other cells: A variety of normal cells was examined by the in situ technique described herein. The production of a deposit around the nuclear periphery was found to be a common occurrence in all normal cells tested. Of special interest was the fact that the normal human lymphocyte (FIG. 4), a non-dividing cell provided from a clinical laboratory, also exhibited a well-defined peripheral deposit of nuclear exposed DNA, thus demonstrating that the present invention is not limited to fibroblasts.

Five other cancers examined all exhibit a decreased genome exposure pattern which was restored after reverse transformation. Three different human neuroblastoma cell lines were utilized: LA-N-1, LA-N-2, and LA-N-5. All can be treated with retinoic acid to produce normal-like neuronal cells. Rat pheochromocytoma PC12 (an adrenal tumor cell line) was treated with nerve growth factor to produce normal sympathetic neuron-like cells. The rat glioma x mouse neuroblastoma hybrid neural tumor line, NG-108-T15, was treated with dibutyryl cyclic AMP to produce nondividing neuronal like cells. For all five cell lines, the untreated cells showed sparse labelling of exposed DNA, whereas the cells treated with the specific inducers gave the intense labelling pattern similar to that exhibited by cyclic AMP-treated CHO-K1 or normal fibroblasts. Thus, the present invention can detect a difference between tumor cells and their normal counterparts in a way that is not cell type specific since similar results are observed with both fibroblasts and neural tumors.

Evidence for existence of DNA regions with different DNase I sensitivities. When the usual protocol for nick translation with DNase I (1-5 minutes) was varied so as to treat the fixed cells for 20 minutes with the enzyme, cytoplasmic structures, presumably mitochondria developed color (FIG. 5C) while the nuclear ring staining decreased markedly in intensity. Moreover, when application of the DNase I was carried out in a separate reaction before the incubation with polymerase and labeled nucleotide, it was possible to demonstrate that as digestion times were increased a decrease in staining of the nuclear periphery and a concomitant increase in staining of an internal subset of chromatin occurred (FIG. 5D). The latter appeared to correspond in size and locale to centromeric chromatin (inset). These results appear to indicate that the nuclear rim DNA is highly sensitive to digestion by the enzyme but that other classes of DNA with different degrees of sequestration exist within the nucleus. This prolonged treatment with DNase I completely removes the most sensitive DNA while gradually nicking more and more of the sequestered subsets.

Effects of other nucleases: Sensitivity of chromatin to digestion by DNase I is thought to involve alterations in nucleosomal structure uniquely detected by certain but not all endonucleases. See Larsen, A., and H. Weintraub, Cell (1982), volume 29, pages 609-622. Some experiments were carried out with other restriction nucleases. Nicking of DNA of interphase CHO-K1 cells with low concentrations of restriction endonucleases EcoR1 (FIG. 5A) or MspI (FIG. 5B) followed by nick translational incorporation of biotin-11-dUTP as a separate incubation step gave a pattern of labeling markedly different from that seen for DNase I. For all concentrations of these endonucleases tested (40-1500 U/ml), incorporation sites appeared distributed throughout the interphase nucleus. Thus, no preferentially labeled areas were seen with these sequence specific reagents (as opposed to conformation specific reagents such as DNase I). Moreover, these enzymes did not produce a labeling differential between control and 8BrcAMP treated cells.

Reproducibility of the reaction Very occasionally, experiments in these various studies failed to produce the expected differences between native CHO-K1 and its reverse transformed state. Thus, in 23 comparisons of the effect of cytoskeletal disruption by colcemid or cytochalasin B on the genome exposure action of 8BrcAMP, 3 failures to secure disappearance of the nuclear ring occurred (FIG. 2). Similarly, in one out of 17 comparisons of the cAMP effect on nuclear matrix localization of exposed DNA (FIG. 3) no effect was seen. These occasional lapses are interpreted as an indication of the failure of current, still relatively crude tissue culture procedures to yield maximal control over the genetic-biochemical cell parameters involved in these intimate regulatory phenomena. We believe, without being limited to theory, that the cellular variability may result from uncontrolled parameters during the in vitro growth period (e.g., different serum lots, media preparation, cell seeding density, culture history of the stock flasks from which individual experiments are seeded, etc.). As such, these considerations would not apply to freshly obtained biopsies which could be tested without in vitro culture.

The present invention lends itself readily to the preparation of kits comprising one or more elements necessary to detect the presence or absence of exposed nuclear DNA. A kit may comprise DNA polymerase I, DNase I, and at least one member selected from the group consisting of the nucleotides dATP, dCTP, dGTP, dTTP and dUTP, at least one of said nucleotides being biotin labeled. Enzymes such as DNase I may be included as a concentrated stock to be diluted before use. A kit may also comprise a detection means for detecting the presence of biotin labeled nucleotides incorporated in exposed nuclear DNA. The kit's detection means may comprise antibiotin antibodies, alkaline phosphatase conjugated antibodies directed against antibiotin antibodies, and amplification reagents or streptavidin-alkaline phosphatase conjugate and amplification reagents. The kit's amplification reagents may comprise nitroblue tetrazolium and 5-bromo-4-chloro-3 indolyl phosphate. The kit may also comprise a slide of fixed normal cells as a positive control and a slide of fixed cancerous cells as a negative control. These slides would be processed along with the cells to be tested in order to give results corresponding to the normal and cancerous situation (i.e., to give positive and negative controls for interpreting the cells to be tested).

It will be appreciated that the instant specification and claims are set forth by way of illustration and not limitation and that various modifications and changes may be made without departing from the spirit and scope of the present invention.

What is claimed is:

1. A method to distinguish between normal and transformed or malignant cells by determining the presence or absence of exposed nuclear DNA in mammalian cells, said method comprising the following steps:

(a) reacting mammalian cells with a reaction mixture comprising DNA polymerase I, DNase I, and at least one member selected from the group consisting of the nucleotides dATP, dCTP, dGTP, dTTP and dUTP, at least one of said nucleotides being labeled, to produce reacted cells;

(b) detecting the presence or absence of labeled nucleotides incorporated in exposed DNA in said reacted cells; and (c) diagnosing for the presence or absence of transformed or malignant cells in said reacted cells, wherein said diagnosing comprises examining the extent and pattern of labelled DNA and comparing said reacted cells with normal cells and cancer cells.

2. The method according to claim 1, wherein said label is biotin or digoxigenin.

3. The method according to claim 2 wherein the biotin labeled nucleotide is biotin-11-dUTP.

4. The method according to claim 2 wherein the biotin labeled nucleotide is biotin-16-dUTP.

5. The method according to claim 19 wherein detecting the presence of biotin labeled nucleotides incorporated in exposed DNA comprises the following steps:

(a) reacting said cells with antibiotin antibodies;

(b) reacting said cells with alkaline phosphatase conjugated antibodies directed against antibiotin antibodies; and (c) reacting said cells with amplification reagents to obtain a color reaction with alkaline phosphatase conjugated antibodies directed against antibiotin antibodies which are specifically bound to incorporated biotinylated nucleotides.

6. The method according to claim 5 wherein said amplification reagents comprise nitroblue tetrazolium and 5-bromo-4-chloro-3 indolyl phosphate.

7. The method according to claim 19 wherein detecting the presence of biotin labeled nucleotides incorporated in exposed DNA comprises the following steps:

(a) reacting said cells with streptavidin-alkaline phosphatase conjugate; and (b) reacting said cells with amplification reagents to obtain a color reacting with streptavidin-alkaline phosphatase conjugates which are specifically bound to incorporated biotinylated nucleotides.

8. The method according to claim 7 wherein said amplification reagents comprise nitroblue tetrazolium and 5-bromo-4-chloro-3 indolyl phosphate.

9. The method according to claim 2, wherein said digoxigenin is digoxigenin-11-dUTP.

10. The method according to claim 2 wherein detecting the presence of digoxigenin labeled nucleotides incorporated in exposed DNA comprises the following steps:

(a) reacting said cells with antidigoxigenin antibodies;

(b) reacting said cells with alkaline phosphatase conjugated antibodies directed against antidigoxigenin antibodies; and (c) reacting said cells with amplification reagents to obtain a color reaction with alkaline phosphatase conjugated antibodies directed against antigigoxigenin antibodies which are specifically bound to digoxigenin labeled nucleotides.

11. The method according to claim 1, wherein said cells are obtained from a fresh biopsy without subsequent in vitro culturing.

12. The method according to claim 1 further comprising the following steps prior to step (a):

(a) precoating coverslips with poly-D-lysine;

(b) seeding said cells onto said coverslips;

(c) placing said coverslips in F12 medium containing 7% fetal calf serum:

(d) rinsing said coverslips twice in phosphate buffered saline;

(e) fixing said coverslips in cold 20:1 methanol: acetic acid;

(f) rinsing said coverslips in PBS.

13. A kit useful for distinguishing between normal and transformed or malignant cells by the method of claim 1, which kit comprises the following:

(a) DNA polymerase I, DNase I, and at least one member selected from the group consisting of the nucleotides dATP, dCTP, dGTP, dTTP and dUPT, at least one of said nucleotides being labeled;

(b) a detecting means for detecting the presence of labeled nucleotides incorporated in exposed nuclear DNA; and (c) a slide of fixed normal cells and a slide of fixed transformed or malignant cells.

14. A kit according to claim 13 wherein said detection means comprises antibiotin antibodies, alkaline phosphatase conjugated antibodies directed against antibiotin antibodies, and amplification reagents.

15. A kit according to claim 12 wherein said detection means comprises streptavidin-alkaline phosphatase conjugate and amplification reagents.

16. A kit according to claims 13 or 14 wherein said amplification reagents comprise nitroblue tetrazolium and 5-bromo-4-chloro-3 indolyl phosphate.

17. The kit according to claim 13, wherein said label is biotin or digoxigenin.

18. A kit according to claim 17 wherein said detection means comprises antigigoxigenin antibodies, alkaline phosphatase conjugated antibodies directed against antidigoxigenin antibodies, and amplification reagents.

19. A kit for distinguishing between normal and transformed or malignant cells by the method of claim 1, which kit comprises DNA polymerase I, DNase I, and at least one member selected from the group consisting of the nucleotides dATP, dCTP, dGTP, dTTP and dUPT, at least one of said nucleotides being labeled.

20. The kit according to claim 19, wherein said label is biotin or digoxigenin.

* * * * *